United States Patent
Pugh et al.

(10) Patent No.: US 8,942,841 B2
(45) Date of Patent: Jan. 27, 2015

(54) LENS STORAGE UNIT WITH PROGRAMMABLE AND COMMUNICATION ELEMENTS FOR MONITORING THE CONDITION OF LENSES AND THEIR RESPONSE TO GEO-SOCIAL PHENOMENA

(75) Inventors: Randall B. Pugh, Jacksonville, FL (US); Edward R. Kernick, Jacksonville, FL (US); Terry O'Brien, Jacksonville, FL (US); Karson S. Putt, Jacksonville, FL (US); James Daniel Riall, St. Johns, FL (US); Andres F. Arrubla, Jacksonville, FL (US)

(73) Assignee: Johnson & Johnson Vision Care, Inc, Jacksonville, FL (US)

( * ) Notice: Subject to any disclaimer, the term of this patent is extended or adjusted under 35 U.S.C. 154(b) by 468 days.

(21) Appl. No.: 13/370,678

(22) Filed: Feb. 10, 2012

(65) Prior Publication Data
US 2013/0144556 A1  Jun. 6, 2013

Related U.S. Application Data

(63) Continuation-in-part of application No. 13/312,167, filed on Dec. 6, 2011.

(51) Int. Cl.
*G06F 11/30* (2006.01)
(52) U.S. Cl.
USPC ............................ 700/117; 700/182
(58) Field of Classification Search
CPC .............................. A61L 12/06; A61L 12/063
See application file for complete search history.

(56) References Cited

U.S. PATENT DOCUMENTS

| | | | |
|---|---|---|---|
| 3,852,032 A | 12/1974 | Urbach | |
| 3,978,341 A | 8/1976 | Hoell | |
| 4,063,890 A | 12/1977 | Baron | |
| 4,868,397 A | 9/1989 | Tittel | |
| 5,120,499 A | 6/1992 | Baron | |
| 5,144,144 A | 9/1992 | Borovsky | |
| 5,178,173 A | 1/1993 | Erickson et al. | |
| 5,439,642 A | 8/1995 | Hagmann | |
| 5,500,732 A * | 3/1996 | Ebel et al. ..................... | 356/124 |
| 5,618,492 A | 4/1997 | Auten | |
| 6,030,554 A | 2/2000 | Ichihara | |
| 6,461,568 B1 | 10/2002 | Eckhardt | |
| 6,566,659 B1 | 5/2003 | Clark | |

(Continued)

FOREIGN PATENT DOCUMENTS

| | | |
|---|---|---|
| DE | 3722384 A | 1/1989 |
| JP | 2002126050 A | 5/2002 |

(Continued)

OTHER PUBLICATIONS

Harris, M.G., et al. "Ultraviolet disinfection of contact lenses." *Optometry and Vision Science*, Oct. 1993;70(10): 839-42. Print.

(Continued)

*Primary Examiner* — Ryan Jarrett

(57) ABSTRACT

The present invention provides for a programmable processor in a ophthalmic lens storage unit for contact lenses. The processor can be in logical connection with a plurality of sensors that can provide data and a digital storage for storing the data and using it via executable software for lens monitoring. In some embodiments, the processor is additionally operative via the executable software to correlate geo-social phenomena with the optical performance of a lens.

27 Claims, 13 Drawing Sheets

(56) References Cited

U.S. PATENT DOCUMENTS

| | | |
|---|---|---|
| 6,592,816 B1 | 7/2003 | Ebel |
| 6,790,409 B1 | 9/2004 | Nakamura |
| 7,217,936 B2 | 5/2007 | Ressler |
| 7,242,997 B2 * | 7/2007 | Geng .......................... 700/117 |
| 7,879,288 B2 | 2/2011 | Brown-Skrobot |
| 8,494,809 B2 * | 7/2013 | Esser et al. ................... 702/182 |
| 2002/0026768 A1 | 3/2002 | Duncan et al. |
| 2004/0234569 A1 | 11/2004 | Nakada |
| 2005/0013729 A1 | 1/2005 | Brown-Skrobot |
| 2005/0028848 A1 | 2/2005 | Lai |
| 2005/0079096 A1 | 4/2005 | Brown-Skrobot et al. |
| 2005/0173652 A1 | 8/2005 | Ressler |
| 2007/0104611 A1 | 5/2007 | Marmo |
| 2007/0206377 A1 | 9/2007 | Borup |
| 2008/0260601 A1 | 10/2008 | Lyon |
| 2009/0086160 A1 | 4/2009 | Enns |
| 2009/0274576 A1 | 11/2009 | Ressler |
| 2010/0141153 A1 | 6/2010 | Recker et al. |
| 2010/0259719 A1 | 10/2010 | Sabeta |
| 2010/0320405 A1 | 12/2010 | Gardner, III |
| 2011/0084834 A1 | 4/2011 | Sabeta |
| 2013/0144743 A1 * | 6/2013 | Pugh et al. ................... 705/26.1 |

FOREIGN PATENT DOCUMENTS

| | | |
|---|---|---|
| JP | 2003093481 A | 4/2003 |
| WO | WO 2011/146497 A | 11/2011 |
| WO | WO 2011/146505 | 11/2011 |
| WO | WO 2012/078744 | 6/2012 |

OTHER PUBLICATIONS

Admoni, M.M., et al. "Disinfection efficacy in an integrated ultraviolet light contact lens care system." *CLAO J.* Oct. 1994; 20(4): 246-8. Print.

Dolman, P.J., et al. "Contact lens disinfection by ultraviolet light." *American Journal of Ophthalmology*, Dec. 15, 1989;108(6):665-9.

"UV Kills These Bugs.", *Review of Optometry*. Dec. 15, 1999 v136 i12 p. 62.

"Device cleans, disinfects soft contact lenses in 15 minutes.", *Ophthalmology Times*., Apr. 15, 2004 v29 i8 p. 66.

International Search Report PCT/US2013/025064 dated May 8, 2013.

* cited by examiner

LENS STORAGE UNIT WITH PROGRAMMABLE AND COMMUNICATION ELEMENTS FOR MONITORING THE CONDITION OF LENSES AND THEIR RESPONSE TO GEO-SOCIAL PHENOMENA

RELATED APPLICATIONS

This application is a continuation-in-part of U.S. patent application Ser. No. 13/312,167 which was filed on Dec. 6, 2011 and entitled "OPHTHALMIC LENS DISINFECTING BASE UNIT WITH PROGRAMMABLE AND COMMUNICATION ELEMENTS," the contents of which are relied upon and incorporated by reference.

FIELD OF USE

This invention describes a case for storing, disinfecting, and monitoring the use of an ophthalmic lens and, more specifically, in some embodiments, programmable and communication elements of a lens storage unit capable of monitoring the condition of said lenses and their response to geo-social phenomena.

BACKGROUND

It is well known that contact lenses can be used to improve vision. Various contact lenses have been commercially produced for many years. Early designs of contact lenses were fashioned from hard materials. Although these lenses are still currently used in some applications, they are not suitable for all patients due to their poor comfort and relatively low permeability to oxygen. Later developments in the field gave rise to soft contact lenses, based upon hydrogels.

Hydrogel contact lenses are very popular today. These lenses are often more comfortable to wear than contact lenses made of hard materials. Many hydrogel contact lenses may be worn for more than one day. However, a build-up of microbial life and bacteria on the lenses generally makes it desirable to periodically remove the lenses and disinfect them.

Disinfection of contact lenses traditionally entails placing the contact lens in a container or case and subjecting the contact lens to a chemical disinfectant. However, chemical disinfectants are not always as efficacious as may be desired. From time to time, a contact lens with a bacterium, mold, fungus or other type of adverse life form is reinserted into a user's eye with the result being a diseased eye.

New methods and approaches are therefore needed to monitor the condition of contact lenses and their response to geo-social phenomena. For example, geo-social phenomena can include changes in weather, remaining use cycles, current lens conditions, age of the user, contamination in a geographic location, etc.

SUMMARY

Accordingly, the present invention includes an ophthalmic lens storage unit with various programming and communicating options to monitor the condition of ophthalmic lenses and correlate changes with geo-social phenomena or eye conditions.

In some embodiments, the ophthalmic lens storage unit is capable of storing reusable contact lenses, disinfecting the lenses during the storage using disinfecting radiation to kill unwanted bacteria, viruses, molds, fungi and the like on a contact lens.

Ophthalmic lens storage units of the present invention include logic to record and analyze data to perform a variety of functions. Functions can include controlling disinfecting radiation during a disinfecting cycle, monitoring lens use, evaluating the optical performance of the lens, and displaying or causing a network associated device to send relevant messages to one or both the user and a third party.

Apparatus of the present invention can include one or more sensors for measuring and storing data descriptive of a condition of the lens. For example, the sensors can measure the optical properties and track the optical performance of the lens to generate a message that alerts the user that the lens must be replaced.

Additionally, in some embodiments a bar code reader can be included to allow the scanning of the package in which the lenses are contained. Upon the scanning of the barcode in the packaging, the disinfecting unit can use a network to download data corresponding to those lenses. For example, data can include, the number of lenses included in package, the recommended length of time or wearing cycles the lenses can be used before replacement, origin, and lot number for the lenses, prescription information, etc.

In other aspects of the present invention, the processor and sensors can additionally be used to monitor the use and conditions of a lens before and after use. For example, a light emitter and detector can be used to measure the optical effect of the lens. The optical effect can be measured prior, during and after disinfecting of the lens is completed to monitor the number of particles that built up in the lens during wear and the effect they have in the lens performance during cleaning. Changes in particle buildup and conditions of the lens can also be stored to detect unusual changes and then alert the user to prevent things, such as for example, an eye infection.

In still other aspects of the present invention, events can be downloaded that are specific to a geographic location or a user. Events can then be assigned a correlation score in relation to the effect it may have in the optical performance of a lens. For example, humidity and pollen changes in the atmosphere, temperature changes, contamination changes, altitude, water contamination, and changes in the duration of cleaning cycles. Event data can be downloaded from $3^{rd}$ party sources such as a lens manufacturer or a weather station according to predetermined settings. Further, measured lens performance data can be stored in relation to the location where the lens wearer is, the data can then be send to the manufacturer for analysis, event effect in other users of lenses, product quality compliance and product development research. Location tracking may take place through the use of the ophthalmic lens storage unit or an associated device. For example, a smart cell phone with an application that records location and altitude.

DETAILED DESCRIPTION OF THE INVENTION

Figure 1:
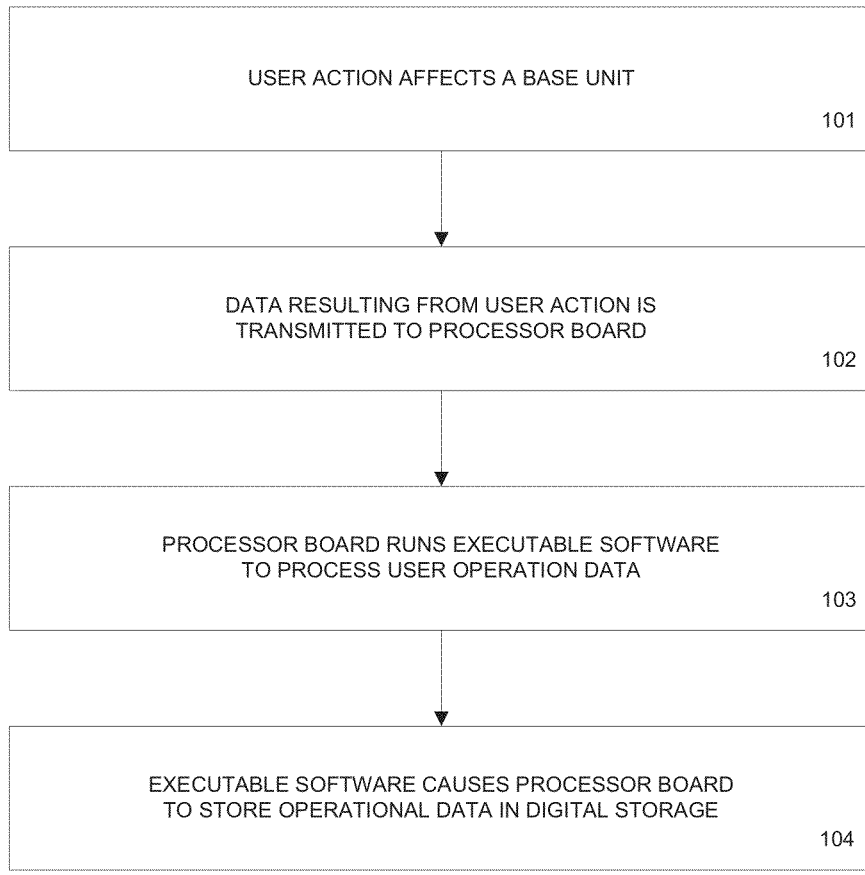
FIG. 1 illustrates method steps for collecting and storing user operation data according to some embodiments of the present invention.

The present invention includes methods and apparatus for storing and analyzing data related to the condition of an ophthalmic lens, for controlling functions of an ophthalmic lens storage unit, data analysis and for displaying messages that result from the data analysis. Also included are options for programming an ophthalmic lens storage unit to communicate with external devices or entities for various purposes. Such as for example, for collection and analysis of geo-social data.

In the following sections detailed descriptions of embodiments of the invention will be given. The descriptions of both preferred and alternative embodiments are exemplary embodiments only, and it is understood by those skilled in the art that variations, modifications, and alterations may be apparent. It is therefore to be understood that said exemplary embodiments do not limit the scope of the underlying invention.

GLOSSARY

In this description and claims directed to the presented invention, various terms may be used for which the following definitions will apply:

Associated Third Party: as used herein refers to a $3^{rd}$ party which may access or send information to the storage unit. For example, it can include an eye care practitioner's office, a contact lens manufacturer, or a retailer.

Authenticating Feature: as used herein refers to readable feature in a lens used to prevent counterfeiting products from being used by a user. For example, the readable feature may be a structural feature, a printed symbol or code.

Automated Order: as used herein refers to an order generated by a processor based on a plurality of factors, including for example, lens use frequency, condition of used lens, user preferences, third party input data, and number of lenses purchased.

Correlated Events: as used herein Correlated Events generally have been evaluated (by the system) and a commonality has been identified between the event and the lens condition for some change in optical performance of the lens.

Correlation Score: as used herein a Correlation Score can be a numerical value from on a scale of how correlated two or more Events/conditions are to each other.

Disinfecting Radiation Dose: as used herein refers to an amount of radiation to reduce an amount of life by at least two logs on a logarithmic scale and preferably three logs or more, wherein life includes at least bacteria, viruses, molds and fungi.

Disinfecting Radiation: as used herein refers to a frequency and intensity of radiation sufficient to diminish the life expectancy of a life form receiving a Disinfecting Radiation Dose.

Event(s): as used herein an Event is generally an occurrence of something that happens regarded of some importance by to the condition of a lens, as predetermined by the specific User or a Pre-determined Third Party. Event data may be formatted in a way that is not specific to its source (e.g. using standard protocols such as XML). The system may also use data from sources such as GPS location for mobile users; weather information; geographical information; local events; time and date; news and current news, as well as the systems current sources (behavioral science, health and wellness, medical, health plan, employer data, etc.).

Geo-Social Data: as used herein Geo-Social Data includes data from the assessment of_locations recorded using location-acquisition technologies (e.g. GPS, phone "check in" applications, etc.) that allow generating life patterns, and which associate user to places they frequently visit. Data includes Normative Data generated in correspondence to the specific location recorded, or to similar locations.

Importance Score: as used herein an Importance Score generally includes a method of prioritizing Events, Acts and lens conditions. For example, it may include the system assigning a numerical value to each specific Event by the system for prioritization.

Lens: refers to any ophthalmic device that resides in or on the eye. These devices can provide optical correction or may be cosmetic. For example, the term lens can refer to a contact lens, intraocular lens, overlay lens, ocular insert, optical insert or other similar device through which vision is corrected or modified, or through which eye physiology is cosmetically enhanced (e.g. iris color) without impeding vision. In some embodiments, the preferred lenses of the invention are soft contact lenses made from silicone elastomers or hydrogels, which include but are not limited to silicone hydrogels, and fluorohydrogels.

Network Access Device: as used herein a Network Access Device means a device for accessing a communications network capable of transforming and receiving digital data.

Normative Data: as used herein Normative Data includes data which represents the normal or average response or impact from any given event, (e.g. news, etc.), across various levels, (e.g. age, sex, etc.), used to compare user specific data with an objective external standard.

Ophthalmic Lens Storing Unit: as used herein refers to a disinfecting base unit, disinfecting storage case, or a combination thereof, capable of storing reusable contact lenses and disinfecting the lenses during the storage. For example, by through the use of a solution and/or receiving disinfecting radiation in a wavelength and intensity suitable to kill unwanted bacteria, viruses, molds, fungi and the like on a contact lens. In some embodiments, the ophthalmic lens storage unit can include more than one storage cases for disinfecting.

Radiation Disinfecting Base Unit: as used herein refers to a device capable of receiving one or more Radiation Disinfecting Storage Cases to provide disinfecting radiation in wavelengths, durations, and intensities suitable to kill unwanted bacteria, viruses, molds, fungi and the like on one or more contact lenses, and in some embodiments, additionally on the surfaces of the disinfecting storage.

Radiation Disinfecting Storage Case: as used herein refers to a lens storage case capable of storing reusable contact lenses and disinfecting the lenses during the storage by receiving disinfecting radiation in a wavelength and intensity suitable to kill unwanted bacteria, viruses, molds, fungi and the like on a contact lens.

Real Time: as used herein Real time means a process, action, or transaction without artificially introduced delay.

Referring now to FIG. 1, a flowchart illustrates exemplary steps that may be used to implement some parts of the present invention. At 101, a user performs an action that affects a ophthalmic lens storage unit. An action may include, for example, opening a radiation disinfecting base unit or case, closing a radiation disinfecting base unit or case, inserting a radiation disinfecting storage case, removing a radiation disinfecting storage case, or pressing a button.

At 102, data resulting from a user action is transmitted to a processor board. Data transmission may include direct electrical connection, such as, for example, via a universal serial buss (USB) or via a wireless transmission, such as for example a radio frequency transmission (RF transmission), Bluetooth, or other mechanism for logical communication.

At 103, a processor board runs executable software to process data resulting from a user's action. In some embodiments, executable software resets a lens disinfecting cycle counter after a user presses a reset button on a ophthalmic lens storage unit to indicate that fresh lenses are being used. In additional embodiments, executable software resets a radiation disinfecting storage case timer after a user presses a reset button on a ophthalmic lens storage unit to indicate a radiation disinfecting storage case has been replaced. Other embodiments include, by way of non-limiting example, executable software incrementing counters for cleaning cycles, timers for lens and storage case usage, and other functions associated with lens and storage case use and disinfection.

At 104, executable software causes a processor board to store data in digital storage. Stored data may include data based on user actions, measurements from sensors, as well as changes resulting from executable software functions such as resetting counters and timers. In some preferred embodiments, stored data includes a date and time associated with a user action or with an executable software action. Data storage may include, for example, user preferred settings, storage in one or more of a historical data log, a current lens data log, and a current radiation disinfecting storage case data log.

Figure 2:
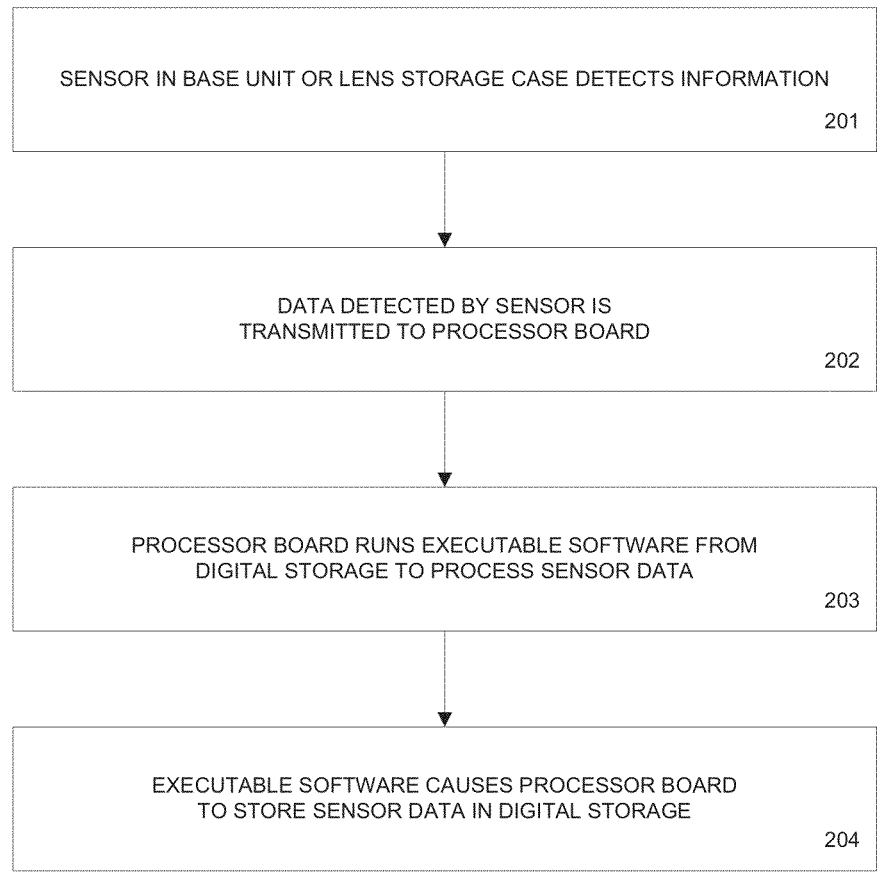
FIG. 2 illustrates method steps for collecting and storing sensor data according to some embodiments of the present invention.

Referring now to FIG. 2, a flowchart illustrates exemplary steps that may be used to implement additional aspects of the present invention. At 201, a sensor in a ophthalmic lens storage unit or a lens storage case detects information. A sensor may include, for example, an LED sensor, a charged couple device (CCD) array, a CCD camera, a barcode scanner, or other known sensor such as, for example a device to detect one or both of a an intensity light and a time duration of exposure to a particular wavelength of radiation, temperature of solution in which the lens is stored, pH of solution in which the lens is stored, moisture, amount of protein build up in the lens, or other condition. At 202, sensor data is transmitted to a processor board. Data transmission may include direct electrical connection, radio frequency transmission, or other mechanism for logical communication or transmission. Although the term transmitted is used to describe the transfer of data from the sensor to the processor board, data may be polled from the sensor or otherwise communicated. Each respective transmission medium will be accompanied by an appropriate transmission device. For example, an RF transmission will include a RF transmitter located within the storage case and a RF receiver in the ophthalmic lens storage unit. Preferred embodiments include both an RF transmitter and receiver in the base and storage case. A direct electrical communication will include a conductive path between the sensor in the storage case and the processor in the base.

At 203, a processor board runs executable software to process sensor data. In some embodiments, sensor data is compared to historical data to determine contact lens or storage case cleanliness. Various embodiments may also include comparison of sensor data to stored baseline data to detect if a radiation disinfecting storage case is present within a radiation disinfecting base unit and to detect if contact lenses are present within a radiation disinfecting storage case. In additional embodiments, sensor data is compared to stored lens profile data, uniquely identifying a contact lens brand. In still other embodiments, sensor data is compared to stored lens data to detect the optical power of each contact lens and thereby identify the right contact lens and the lens contact lens to assist the user of the disinfecting unit.

For example, in some embodiments, a predetermined amount of ultraviolet (UV) radiation may be passed through a contact lens stored in the storage case. One or more sensors may be used to detect amounts of UV radiation passing through one or more portions of the contact lens. A profile may be generated of amounts of radiation passing through the one or more portions. Particular types of lenses will generate identifiable patterns in the profiles. The patterns may be used to identify a type of lens, disinfection rate for the specific lens, or even identify a specific lens type.

At 204, executable software causes a processor board to store data in digital storage. Stored data may include data collected by sensors as well as data resulting from executable software analysis such as, for example, a number of days until lenses should be replaced, a number of days until a storage case should be replaced, a percentage of lens opacity indicating lens cleanliness, a percentage of radiation disinfecting storage case opacity indicating radiation disinfecting storage case cleanliness, presence or absence of radiation disinfecting storage case, presence or absence of contact lenses, identified lens brand, and identified lens optical powers. In some preferred embodiments, stored data includes a date and time associated with sensor data or with results from executable software. Data storage may include, for example, storage in one or more of a historical data log, a current lens data log, a current radiation disinfecting storage case data log, and a sensor-specific data log.

Figure 3:
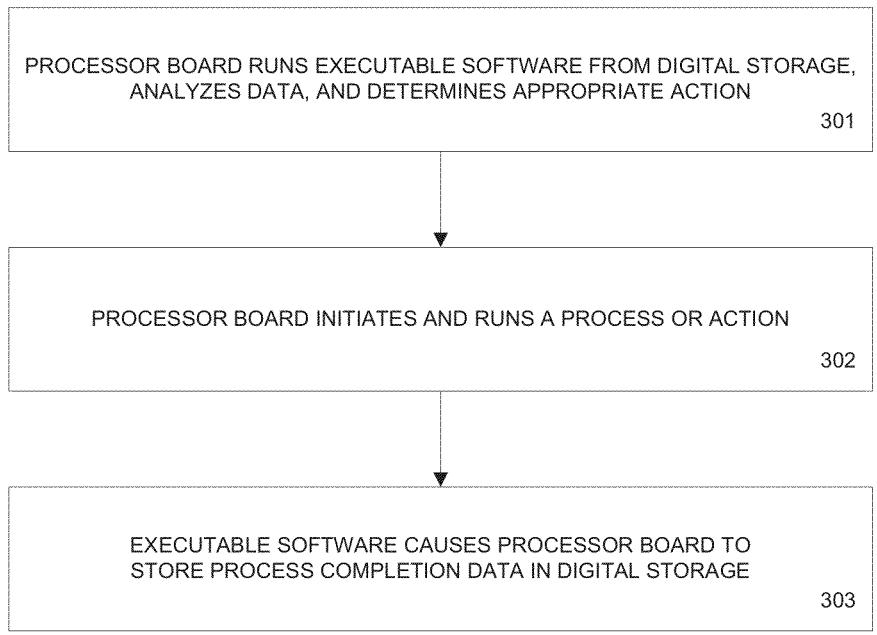
FIG. 3 illustrates method steps for running a process or action, thereby controlling case functions, according to some embodiments of the present invention.

Referring now to FIG. 3, a flowchart illustrates exemplary steps that may be used to implement additional aspects of the present invention. At 301, a processor board runs executable software to analyze previously stored data and/or data received from an associated device and determines an appropriate action. In some embodiments of the present invention, executable software analyzes whether a ophthalmic lens storage unit has recently been plugged in or been closed, the current state of the lens, and relevant events. In other embodiments, executable software analyzes stored data to determine when a cleaning cycle should be started. Specific details such as the duration, pattern, and intensity of disinfecting radiation used in a cleaning cycle are calculated or selected in some embodiments of the present invention. In other aspects of the present invention, executable software identifies whether a radiation disinfecting base unit is currently plugged into an external power source.

At 302, a processor board runs a process or action, such as by way of non-limiting example, a radiation disinfecting base case initialization routine and a radiation disinfecting cleaning cycle. Other actions can include, for example, sending a message warding to the user/associated $3^{rd}$ party and send measured data to a server among others. Other embodiments include power management actions such as charging a battery in a ophthalmic lens storage unit, running the ophthalmic lens storage unit from battery power or running the base unit from direct power.

At 303, executable software causes a processor board to store process completion data in digital storage. Process completion data may include, for example, data related to case initialization processes, including detection of LED strength, detection of presence of radiation disinfecting storage case, detection of contact lenses within radiation disinfecting storage case, and detection of correct contact lens powers in each well of a radiation disinfecting storage case. In other aspects of the present invention, stored data may be related to a radiation disinfecting cleaning cycle including duration of radiation, pattern of radiation timing, radiation intensity, and post-disinfection cleanliness data pertaining to contact lenses and radiation disinfecting storage case. In still other embodiments, completion data includes battery charging time, percent battery full, time periods in which base case was operated using a battery and in which base case was operated using direct power. In some preferred embodiments, stored data includes a date and time associated with process completion data. Data storage may include, for example, storage in one or more of a historical data log, a current lens data log, and a current radiation disinfecting storage case data log.

Figure 4:
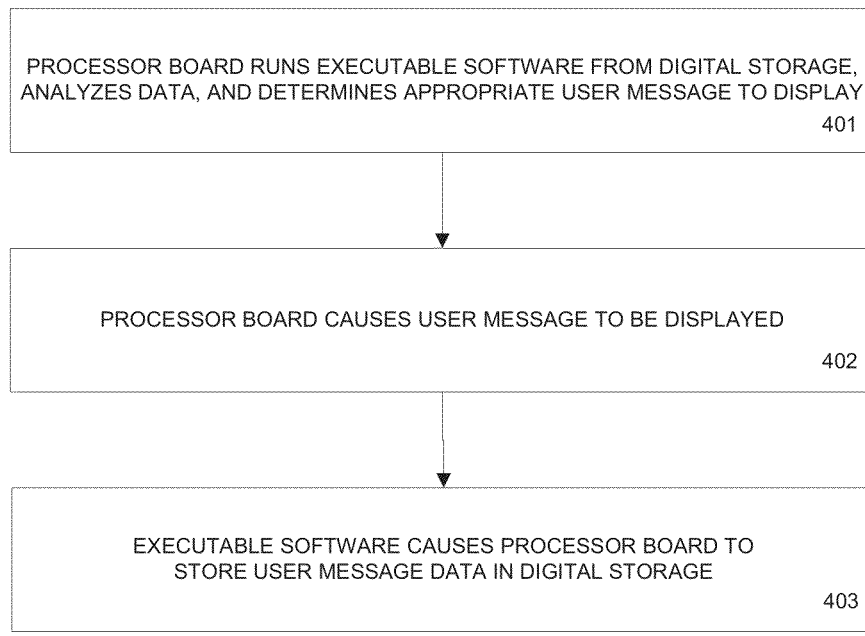
FIG. 4 illustrates method steps for displaying user messages according to some embodiments of the present invention.

Referring now to FIG. 4, a flowchart illustrates exemplary steps that may be used to implement additional aspects of the present invention. At 401, a processor board runs executable software to analyze previously stored data and determines an appropriate user message to be displayed. In some embodiments of the present invention, executable software analyzes, for example, the remaining life of the lens, the need for an appointment with an eye care practitioner, remaining lenses, ordering information and automated ordering, tracking of lenses using a barcode to ensure lenses are not counterfeit lenses, optical performance of the lens and recommendations of new products for the specific user.

At 402, a processor board causes a user message to be displayed on a message display area of a ophthalmic lens storage unit. Some embodiments include messages indicating it is time to insert and disinfect contact lenses, it is time to begin using a new pair of contact lenses, it is time to begin using a new radiation disinfecting storage case, it is time to make an annual appointment with the user's eye care professional, it is time to order new lenses, and new product information specific to the user. In other embodiments, warning messages are displayed, for example, a disinfecting cycle was interrupted, a disinfecting cycle did not complete properly, bar code is not recognized/match the lens per the database and the user should contact a customer service representative, a user has mixed up their right and left contact lenses by placing lenses in the wrong wells of a radiation disinfecting storage case, a user should see their eye care professional soon, as for example, when an unusually high buildup of microbes on lenses has been detected. Still other embodiments include base unit status messages such as, for example, current battery level, battery needs to be recharged, there is not enough battery to complete a cleaning cycle so unit must be plugged in, battery can no longer be recharged so it is time to replace the radiation disinfecting base unit, one or more LEDs are decaying so it is time to replace the radiation disinfecting base unit. Further embodiments can include instructional messages such as how to resume a disinfecting cycle, how to restart a disinfecting cycle, how to reprogram a radiation disinfecting base unit, how to store data on a computer or other external device, and how to send data to an eye care professional or other party.

At 403, executable software causes a processor board to store user message data in digital storage. User message data may include, for example, an indication of a specific message displayed and a reason that triggered the specific message. For example, a message to change a contact radiation disinfecting storage case may be triggered because a time limit has been reached or because a sensor detected a change indicator on a radiation disinfecting storage case. In some preferred embodiments, stored data includes a date and time associated with user message display. Data storage may include, for example, storage in one or more of a historical data log, a current lens data log, and a current radiation disinfecting storage case data log.

Figure 5:
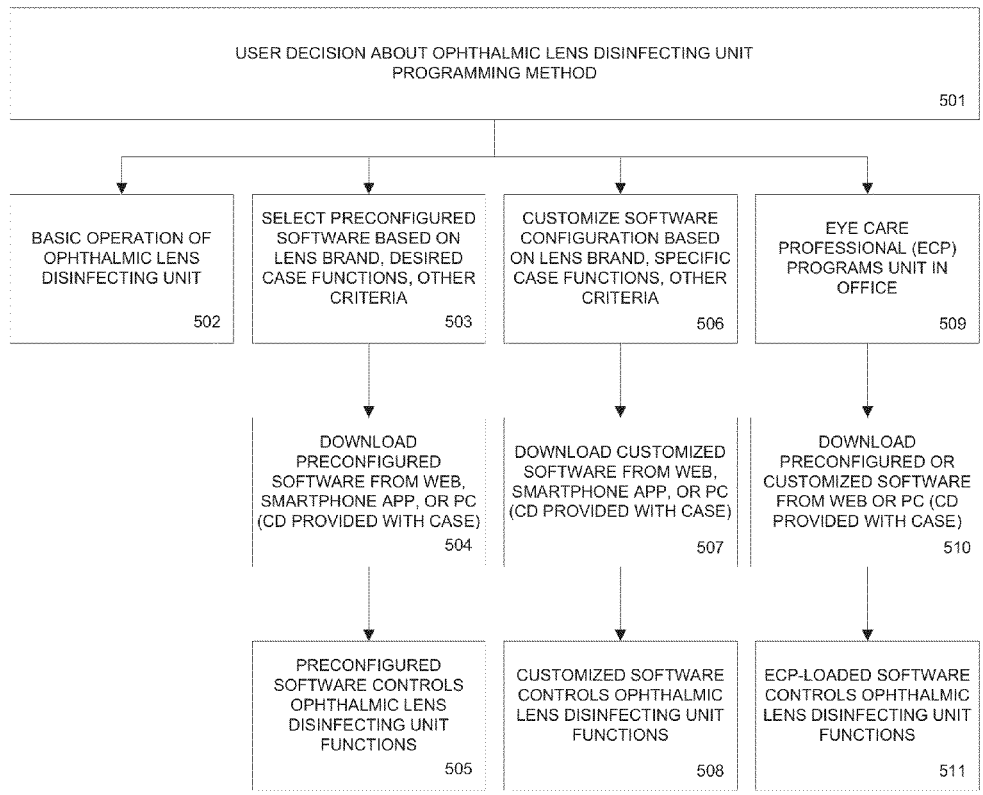
FIG. 5 illustrates method steps for programming an Ophthalmic Lens Storage Unit.

Referring now to FIG. 5, a flowchart illustrates exemplary steps that may be used to implement additional aspects of the present invention. At 501, a user determines how to program an ophthalmic lens storage unit by selecting specific setting options. The user decision may be based on information provided through the ophthalmic lens storage unit, information available on a website, information from their eye care professional, information from lens manufacturer or other source. The user decision leads to 502, 503, 506 or 509. A user may download different preconfigured or customized software at any time. A new software download may be desirable if a user's lens brand or lens parameters change, if updated software is available to correct program errors, if the user desires more or less functionality from the ophthalmic lens disinfecting unit, and for other reasons. After loading a preconfigured or customized program, a user may or may not be provided with an option to revert their ophthalmic lens storage unit to its basic operational state.

At 502, a user decides to use only basic functions provided with an ophthalmic lens storage unit. No additional steps, programming, or configuration are necessary to use the unit with base functionality. Basic operation may include, by way of non-limiting example, initialization routine when user closes case, generic radiation disinfecting cycle appropriate for many disposable lenses, and basic user messages.

At 503, a user selects from a limited number of preconfigured software options for an ophthalmic lens storage unit. Preconfigured software may be selected, for example, on the basis of the lens brand worn by the user, on desired case functions, and other criteria. At 504, selected preconfigured software is downloaded to an ophthalmic lens storage unit from a website, a Smartphone application, a PC using a CD provided with an ophthalmic lens storage unit, or other known method of software distribution. At 505, an ophthalmic lens storage unit is controlled using preconfigured software. In addition to the functions available in basic operation, preconfigured software may support, by way of non-limiting example, radiation disinfecting cycles specific to a contact lens brand and wear schedule, counters and reminders based on standard lens wear schedules, ability to later upload data from ophthalmic lens storage unit for analysis, expanded user messages, and other functions.

At 506, a user customizes software configuration for an ophthalmic lens storage unit. Software may be customized, for example, by selecting specific brand and lens parameters worn by a user for each eye, by selecting custom lens wear schedules, by selecting or blocking functions such as counters and reminders, by entering date of last eye exam or lens purchase to enable reminder for subsequent eye exams or lens purchases, by entering a name or other identifying information, by selecting data communication options, by scanning a bar code in the packaging of the lens to download specific information about the lens, and other functions. At 507, customized software is downloaded to an ophthalmic lens disinfecting unit from a website, a Smartphone application, a PC using a CD provided with an ophthalmic lens storage unit, or other known method of software distribution. At 508, an ophthalmic lens storage unit is controlled using customized software. In addition to the functions available in basic operation, customized software may support, by way of non-limiting example, radiation disinfecting cycles specific to a contact lens brand and parameters worn by a user, counters and reminders based on lens wear schedule indicated by a user, ability to identify wrong contact lens powers in wrong wells of storage case, ability to later upload data from ophthalmic lens disinfecting unit for analysis, customized user messages, display of user name or other identifying information, communication of data to other devices, and other functions.

At 509, an eye care professional (ECP) programs an ophthalmic lens storage unit in the office for a user. An ECP may use preconfigured software as described in the path starting at step 503, or may use customized software configuration as described in the path starting at step 506. At 510, preconfigured or customized software is downloaded to an ophthalmic lens storage unit from a website, a Smartphone application, a PC using a CD provided with an ophthalmic lens storage unit, or other known method of software distribution. At 511, an ophthalmic lens storage unit can be controlled using preconfigured software as described previously in step 505, or customized software as described previously in step 508.

Figure 6:
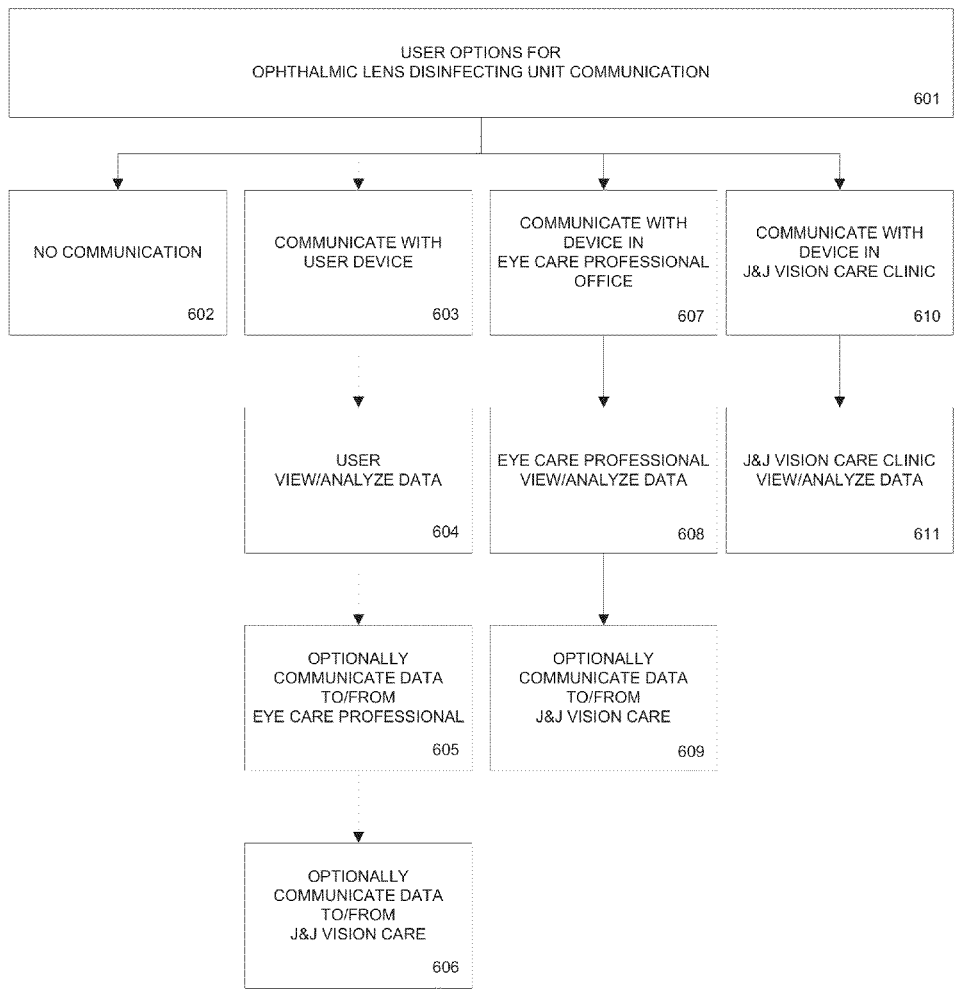
FIG. 6 illustrates method steps for communicating data between an Ophthalmic Lens Storage Unit and other devices and entities.

Referring now to FIG. 6, a flowchart illustrates exemplary steps that may be used to implement additional aspects of the present invention. At 601, a user may make a decision about communicating data from an ophthalmic lens storage unit. Alternatively, a default communication may be implemented The user decision may be based, for example, on information provided with an ophthalmic lens storage unit, information available on a website, information from their eye care professional, or other source. One or both of a user decision and a default communication mode eventually can lead to 602, 603, 607 or 610.

At 602, a user decides to use an ophthalmic lens storage unit in a stand-alone manner. In various implementations, data may be stored for subsequent analysis or simply not recorded.

At 603, a user enables communication between an ophthalmic lens storage unit and a user device such as a PC, Smartphone, or other device capable of receiving ophthalmic lens storage unit data. In some preferred embodiments, an ophthalmic lens disinfecting unit application available via a PC, Smartphone or other device facilitates the sharing of data. An ophthalmic lens storage unit application may be a standalone application running on a computing device, may be an application available on a website accessed using a computing device, or may be a distributed application with functions running on a both standalone computing device and a website.

At 604, an ophthalmic lens storage unit application is used to view and analyze ophthalmic lens disinfecting unit data. In some embodiments, data includes text, charts, graphs, and other representations. Data may include, by way of non-limiting example, contact lens brand and parameters, contact lens wear schedules, user specific information, cleaning cycle details, contact lens cleanliness data, contact lens and radiation disinfecting storage case replacement history, number of days until recommended contact lens replacement, number of days until recommended radiation disinfecting storage case replacement. Other embodiments include ophthalmic lens storage unit diagnostic information, such as, for example, battery information, LED information, sensor information, and communication details.

At 605, a user makes a decision to send ophthalmic lens storage unit data to an eye care professional. In some preferred embodiments, an ophthalmic lens storage unit application facilitates the sharing of data with an eye care professional using known data transmission methods, such as, for example, sending an email containing text information, sending an email containing a data file, making a file or data available on a website to which the eye care professional has access, or other means. Ophthalmic lens storage unit data shared with an eye care professional may include, by way of non-limiting example, contact lens brand and parameters, contact lens wear schedules, user specific information, cleaning cycle details, contact lens cleanliness data, contact lens and radiation disinfecting storage case replacement history, number of days until recommended contact lens replacement, number of days until recommended radiation disinfecting storage case replacement. Other embodiments may include the sharing of ophthalmic lens storage unit diagnostic information, such as, for example, battery information, LED information, sensor information, and communication details. Shared data may be in the form of text, charts, graphs, and other representations. In another aspect, in some embodiments, an eye care professional may also be capable of transmitting messages and data to a user's ophthalmic lens storage unit application, where it may be viewed in the application or may be transmitted to an ophthalmic lens disinfecting unit and displayed on the display area. Eye care professional messages and data may include, for example, eye exam reminders, contact lens purchase reminders, sale information, ordering information, or other information.

At 606, a user makes a decision to send ophthalmic lens storage unit data to a contact lens manufacturer or other provider of contact lenses. In some preferred embodiments, an ophthalmic lens storage unit application facilitates the sharing of data with a manufacturer or other provider of contact lenses using known data transmission methods, such as, for example, sending an email containing text information, sending an email containing a data file, making a file or data available on a website to which the manufacturer or other provider of contact lenses has access, or other means. Ophthalmic lens storage unit data shared with a manufacturer or other provider of contact lenses may include, by way of non-limiting example, contact lens brand and parameters, contact lens wear schedules, user specific information, cleaning cycle details, contact lens cleanliness data, contact lens and radiation disinfecting storage case replacement history, number of days until recommended contact lens replacement, number of days until recommended radiation disinfecting storage case replacement. Other embodiments may include the sharing of ophthalmic lens storage unit diagnostic information, such as, for example, battery information, LED information, sensor information, and communication details. Shared data may be in the form of text, charts, graphs, and other representations. In another aspect, in some embodiments, a manufacturer or other provider of contact lenses may also be capable of transmitting messages and data to a user's ophthalmic lens storage unit application, where it may be viewed in the application or may be transmitted to an ophthalmic lens storage unit and displayed on the display area. Manufacturer messages and data may include, for example, eye exam reminders, contact lens purchase reminders, ordering information, instructions for completing an automated order, contact lens rebate information, contact lens purchase coupons, or other information.

At 607, a user provides an ophthalmic lens storage unit to an eye care professional, who enables communication from the ophthalmic lens disinfecting unit to a device in the eye care professional office such as a PC, Smartphone, or other device capable of receiving ophthalmic lens storage unit data. In some preferred embodiments, an ophthalmic lens storage unit application available via a PC, Smartphone or other device facilitates the sharing of data. An ophthalmic lens storage unit application may be a standalone application running on a computing device, may be an application available on a website accessed using a computing device, or may be a distributed application with functions running on a both standalone computing device and a website. At 608, an ophthalmic lens storage unit application is used to view and analyze ophthalmic lens storage unit data. In some embodiments, data includes text, charts, graphs and other representations. Data may include, by way of non-limiting example, contact lens brand and parameters, contact lens wear schedules, user specific information, cleaning cycle details, contact lens cleanliness data, contact lens and radiation disinfecting storage case replacement history, number of days until recommended contact lens replacement, number of days until recommended radiation disinfecting storage case replacement. Other embodiments include ophthalmic lens storage unit diagnostic information, such as, for example, battery information, LED information, sensor information, and communication details. In another aspect, in some embodiments, an eye care professional may also be capable of transmitting messages and data to a user's ophthalmic lens storage unit, where it may be displayed on the display area. Eye care professional messages and data may include, for example, eye exam reminders, contact lens purchase reminders, and sale information.

At 609, an eye care professional makes a decision to send ophthalmic lens storage unit to a contact lens manufacturer or other provider of contact lenses. In some preferred embodiments, an ophthalmic lens storage unit application facilitates the sharing of data with a manufacturer or other provider of contact lenses using known data transmission methods, such as, for example, sending an email containing text information, sending an email containing a data file, making a file or data available on a website to which the manufacturer or other provider of contact lenses has access, or other means. Ophthalmic lens storage unit data shared with a manufacturer or other provider of contact lenses may include, by way of non-limiting example, contact lens brand and parameters, contact lens wear schedules, user specific information, cleaning cycle details, contact lens cleanliness data, contact lens and radiation disinfecting storage case replacement history, number of days until recommended contact lens replacement, number of days until recommended radiation disinfecting storage case replacement. Other embodiments may include the sharing of ophthalmic lens storage unit diagnostic information, such as, for example, battery information, LED information, sensor information, and communication details. Shared data may be in the form of text, charts, graphs, and other representations.

At 610, a user provides an ophthalmic lens storage unit to a manufacturer or other provider of contact lenses eye care professional, who enables communication from the ophthalmic lens storage unit to a device in the manufacturer office such as a PC, Smartphone, or other device capable of receiving ophthalmic lens storage unit data. In some preferred embodiments, an ophthalmic lens storage unit application available via a PC, Smartphone or other device facilitates the sharing of data. An ophthalmic lens storage unit application may be a standalone application running on a computing device, may be an application available on a website accessed using a computing device, or may be a distributed application with functions running on a both standalone computing device and a website. At 611, an ophthalmic lens storage unit application is used to view and analyze ophthalmic lens storage unit data. In some embodiments, data includes text, charts, graphs and other representations. Data may include, by way of non-limiting example, contact lens brand and parameters, contact lens wear schedules, user specific information, cleaning cycle details, contact lens cleanliness data, contact lens and radiation disinfecting storage case replacement history, number of days until recommended contact lens replacement, number of days until recommended radiation disinfecting storage case replacement. Other embodiments include ophthalmic lens storage unit diagnostic information, such as, for example, battery information, LED information, sensor information, and communication details. In another aspect, in some embodiments, a manufacturer or other provider of contact lenses may also be capable of transmitting messages and data to a user's ophthalmic lens storage unit where it may be displayed on the display area. Manufacturer messages and data may include, for example, eye exam reminders, contact lens purchase reminders, contact lens rebate information, contact lens purchase coupons, or other information.

Figure 7:
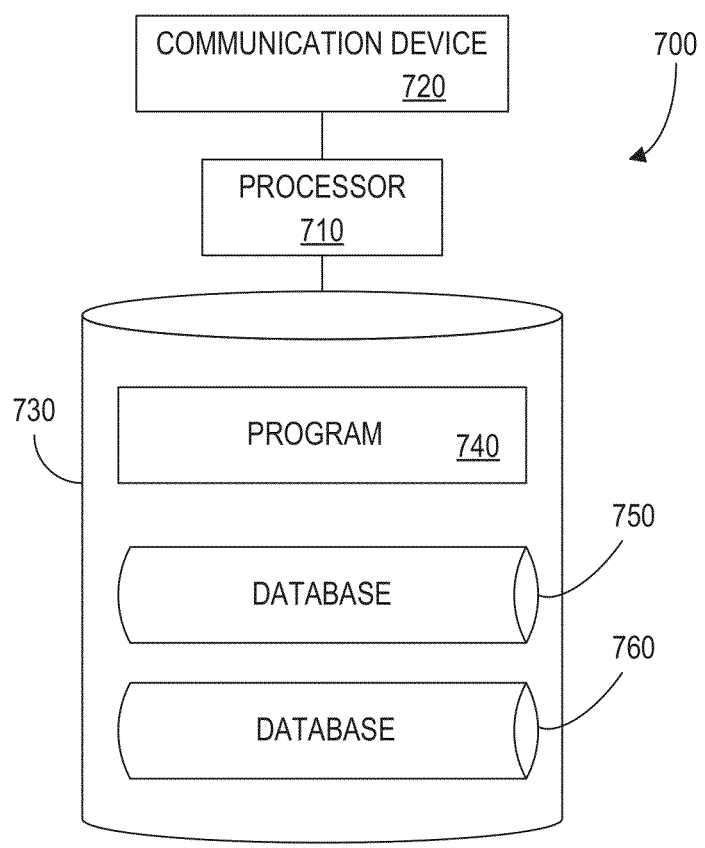
FIG. 7 illustrates a processor that may be used in some embodiments of the present invention.

Referring now to FIG. 7 a controller 700 that may be used in some embodiments of the present invention is illustrated. The controller 700 includes a processor 710, which may include one or more processor components coupled to a communication device 720. The communication device 720 may also be configured to communicate information via a communication channel to electronically transmit and receive digital data related to the functions discussed herein.

The communication device 720 may also be used to communicate, for example, with one or more human readable display devices, such as, for example: an LCD panel, a LED display or other display device or printer. In some preferred a touch screen is utilized providing a human interface with the ophthalmic lens storage unit.

The processor 710 may also be in communication with a storage device 730. The storage device 730 may comprise any appropriate information storage device, including combinations of magnetic storage devices (e.g., magnetic tape, radio frequency tags, and hard disk drives), optical storage devices, and/or semiconductor memory devices such as Random Access Memory (RAM) devices and Read-Only Memory (ROM) devices.

The storage device 730 can store a program 740 for controlling the processor 710. The processor 710 performs instructions of the program 740, and thereby operates in accordance with the present invention. For example, the processor 710 may receive information descriptive of lens, lens inventory, lens optical performance, eye care practitioner's office prescription or appointment information, user's preferences, and the like. The storage device 730 can also store patient related data received, from sources such as the eye care practitioner's office, directly from the manufacture's network, a third party, or imputed by the user, in one or more databases 750 and 760.

Figure 8:
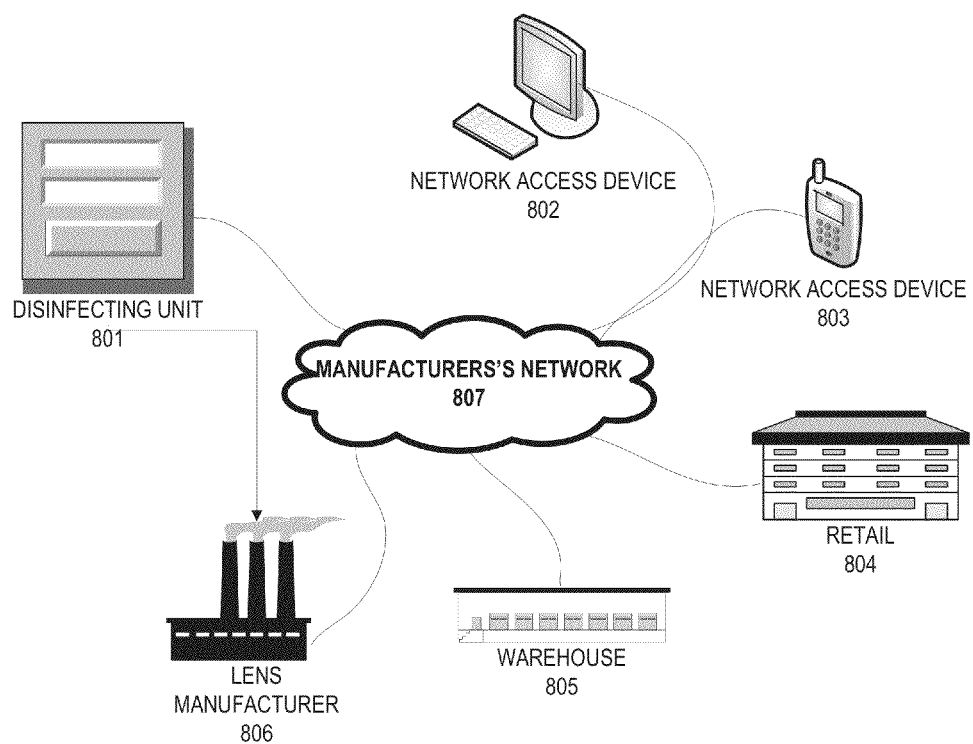
FIG. 8 illustrates a network diagram with devices that may be used for Automated Ordering in some embodiments of the present invention.

Referring now to FIG. 8, a network diagram illustrates how an ophthalmic lens storage unit 801 may be connected via a the manufacture's network 807, such as, for example, the Internet, a cellular link, a virtual private network or other vehicle for transferring digital data. The ophthalmic lens storage unit may include sensors, communicating devices, and programmed capabilities such as the ones described in this application. In addition, the apparatus may include a programmable processor and storage device connected to a human readable display device, as discussed further below in regard to FIG. 7.

Generally, the ophthalmic lens storage unit 801 can be functional to track an inventory accessible by the ophthalmic lens storage unit 801 and to generate an automated order for ophthalmic lenses based on a plurality of stored inputs in the memory. The automated order can be programmed to be sent along with payment information, for example to a manufacturer plant, or retailer upon the confirmation by the user. In some preferred embodiments, the memory in the ophthalmic lens storage unit 801 may include information about the user, user's eye care practitioner, user's purchased lenses, number of lenses remaining, weather and user's prescription. Furthermore, when lenses are received by the user, a bar code in the packaging may be scanned with some ophthalmic lens storage units to provide digital data descriptive of the lenses/order.

Digital data may be processed by storing the data within the ophthalmic lens storage unit 801 or transmitted to a destination 802-806 connected to the distributed network 807. This data can be useful to track specific orders of lenses, prevent any use of counterfeit lenses which can be harmful to the user, track user feedback pertaining to the specific lenses, facilitate the recall of any specific product by alerting the user before any negative result can occur, ensure compliance with eye care practitioner's prescribed product, and track effects of weather conditions with specific lenses. In addition, weather information and allergy alerts data may be downloaded by the device for message generation and data analysis. Data analysis can include for example, correlating weather and allergy information with abnormal protein or microbial buildup.

A destination 802-806 can include, for example, a network access device 802 that includes a display and keyboard accessing the distributed network 807 under the control of a processor. The network access device may therefore include a personal computer, mobile device, laptop, or terminal. Other network access devices 803 may be mobile in nature and include personal digital assistants ("PDA"s), cellular phones with network access capabilities, net books, or other relatively small processor run appliances with the ability to send and receive digital data across a network.

Still other embodiments may include network access devices 804-805 associated with a retail location for ophthalmic lenses and solutions, a warehouse for ophthalmic lenses and solutions and an ophthalmic lens and solutions manufacturing facility.

The ophthalmic lens storage unit 801 may therefore receive information about ophthalmic lenses and solutions to assist the user of the device in tracking the use of the lenses, placing automated orders directly to the manufacturing facility, tracking eye care practitioner ("ECP") appointments, and comparing bar code data and lens compliance to detect and signal counterfeit lenses that may not meet health standards and cause significant eye problems. For example, digital data descriptive of which manufacturing plant of the lenses, expiration dates, and optical power specifications. The automated ordering may also be transmitted from the ophthalmic lens storage unit 801 and to any network access device 802-806. The digital data may be transmitted one or both of: with no artificial delay introduced (real time), or on a periodic basis.

In some embodiments, the ophthalmic lens storage unit 801 compiles a report descriptive of an aggregate of lenses used by the user and transmits the report to network access devices associated with related entity. The related entity can be, for example, a lens manufacturer, a market analyst, an ophthalmic lens retailer; an ophthalmic lens warehouse, or other interested entity.

In some embodiments, a ophthalmic lens storage unit 801 may be functional to analyze data specific to the user and suggest things such as, for example, more trial lenses and solutions to a patient and also initiate an order for commercially available lenses. Initiation of an order may include transmission of digital data descriptive of the patient and lenses and solutions to be shipped to the patient. The digital information initiating may therefore include, for example, any or all of the following: patient name and address, billing information, payment information, lens SKU, quantity of lenses, eye care practitioner providing prescription for the lenses, weather and allergy data and any other information generally received by an online retail site for lens sales. One exemplary online sales vehicle includes Acuvue-Direct™ which processes orders for ophthalmic lenses via a distributed network 807 which includes the Internet.

In another aspect, a ophthalmic lens storage unit 801 may be functional to initiate an automated reminder, such as ACU-MINDER™, to replace the patient's contact lenses after the time of recommended wear has been completed. A schedule may commence based upon the type of lens dispensed and a suggested lens wearing schedule or based on data gathered from measurement of the sensors in the ophthalmic lens storage unit. The ophthalmic lens storage unit 801 may then automatically display a reminder in the user interphase or cause to transmit a reminder, such as, for example, via one or more of: email, text message, social media, RSS, and telephone. The reminder can include a human interpretable message that instructs them to do a specific action, such as replace their lenses.

Figure 9:
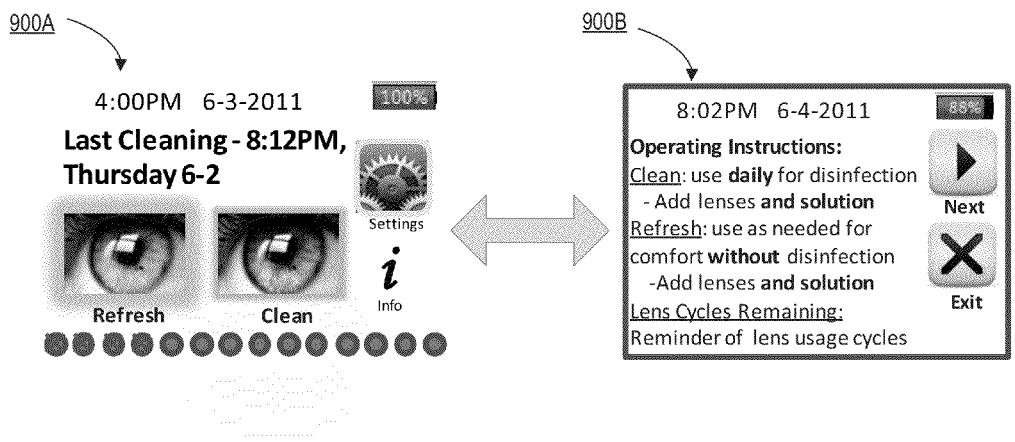
FIG. 9 illustrates exemplary screen shots of the touch screen display, of a disinfecting unit device depicting possible user options of the device.

Referring now to FIG. 9, exemplary screen shots of the touch screen display of a ophthalmic lens storage unit are depicted. Screen shot 900A of the ophthalmic lens storage unit display depicts exemplary options a user would see in the display for the lens disinfecting cycle. The software in the disinfecting base unit can show the user when his last cleaning was and how many cycles remain in the lifetime for the specific lens. Additionally, the user can see the battery life remaining in the ophthalmic lens storage unit, user settings, which in some embodiments control the disinfection process to a specified time by changing the intensity of the UV and time of exposure, and other functions as they may be programmed in the device. Further, more information about each process, instructional information, or informative data may be provided to the user. For example, as depicted in screen shot 900B operating instructions that can include different functionality of the ophthalmic lens storage unit.

Figure 10:
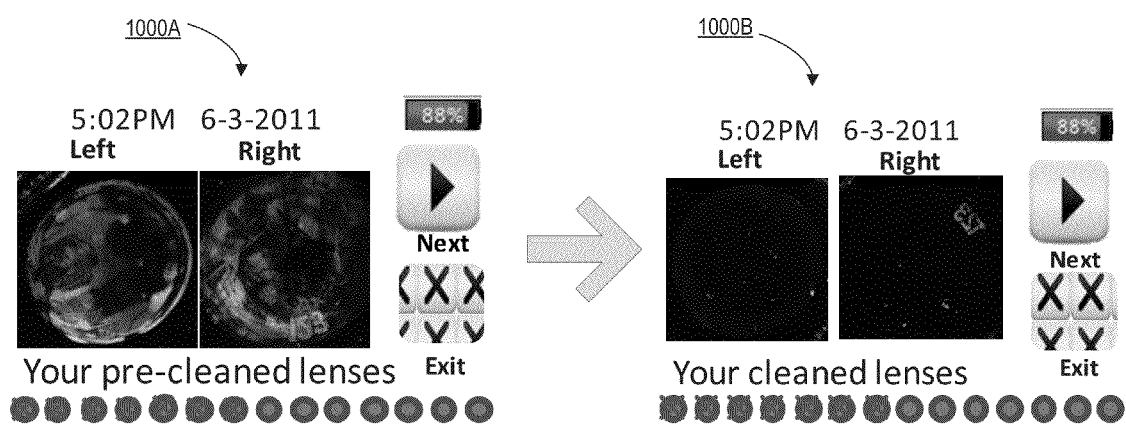
FIG. 10 illustrates exemplary screen shots of a disinfecting base unit depicting a pre-cleaned lens and cleaned lens as measured by sensors that may be incorporated in an Ophthalmic Lens Storage Unit.

Referring now to FIG. 10, exemplary screen shots of a ophthalmic lens storage unit showing a measured pre-cleaned lens and cleaned lens are depicted. At 1000A, the sensors and program may generate an image projected in the touch screen of the ophthalmic lens storage unit showing a left lens and right lens prior to disinfecting for the user to see. More importantly, the program may take the digital data gathered by the sensors to track the amount of protein buildup or germs present prior to cleaning. This stored digital data may be analyzed to alert the user when there is a change, in particle buildup or specific germs, greater than what would be normal in relation to preprogrammed thresholds. Upon detecting an abnormal amount of protein buildup or germs in the lens, the ophthalmic lens storage unit may alert the user, send a picture directly to the eye care practitioner, or cause a specific message to be send to the user through one of the associated network devices discussed in FIG. 8.

Additionally, as depicted the screen shot 1000B the ophthalmic lens storage unit can also analyze and generate digital data to determine when the lens is not undergoing the desired cleaning. For example, this may happen when the lens becomes defective, when the lifespan of the lens has ended, the particle buildup is abnormal, or when a lens has expired. Inadequacy in the disinfecting may be determined, for example, by tracking the rate in which particles come off from the lens and programming thresholds.

Figure 11:
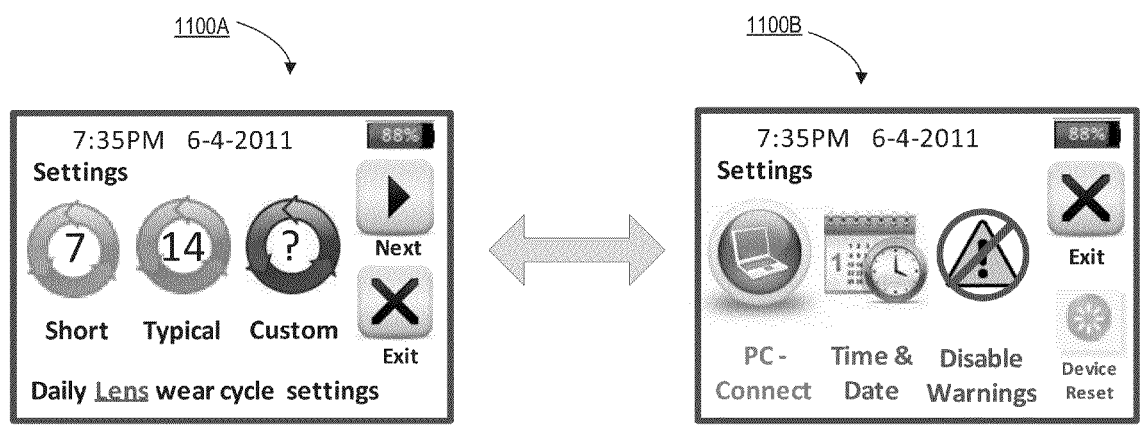
FIG. 11 illustrates exemplary screen shots of a disinfecting unit device depicting some of the user settings to customize the functionality of an Ophthalmic Lens Storage Unit.

Referring now to FIG. 11, exemplary screen shots of a ophthalmic lens storage unit depicting additional user settings that can be included in the device are depicted. At 1100A, exemplary settings associated with the lens wear cycle are shown as depicted by the user interphase. These settings can include the user's preferences as to the duration of the cycle. This, as explained in other sections of this disclosure, can cause the program to vary the intensity of the disinfecting radiation, the duration of each dose of radiation and the frequency between said doses of radiation.

At 1100B, user's settings for networks that may be associated with the ophthalmic lens storage unit as described in FIG. 8 are included. In addition, time and date user settings which allow the user to change it manually or to link it to a network device, for example, a cell phone, for automatic date/time changes during traveling, or during daytime saving time changes. In addition, weather information and allergy alerts data may be downloaded by the device for message generation and data analysis. Data analysis can include for example, correlating weather and allergy information with abnormal protein or microbial buildup. Warnings may also be controlled to prevent unwanted alerts to the user.

Figure 12:
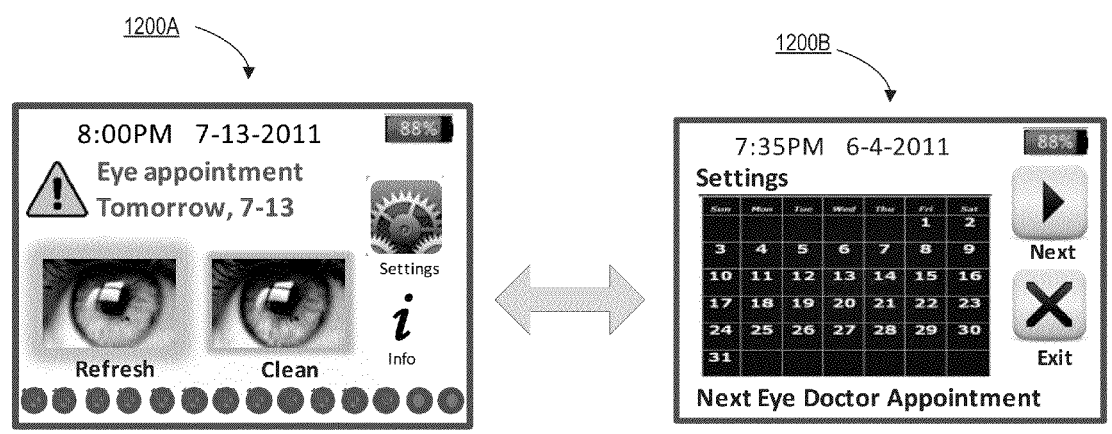
FIG. 12 illustrates exemplary screen shots of a disinfecting base unit device associated with Eye Care Practitioner Appointments and Automated Lens Ordering.

Referring now to FIG. 12, exemplary screen shots of a ophthalmic lens storage unit associated with Eye Care Practitioner Appointments and Automated Lens Ordering are shown. At 1200A, the screen is showing a reminder to attend a scheduled eye appointment. The ophthalmic lens storage unit can further cause a network associated device to send additional information about the reminder, for example, directions to the location, cancellation information, etc. After attending the appointment, the user can check off through the interface that he/she has attended the appointment and the ophthalmic lens storage unit may record and use this data to track and schedule future appointments. Alternatively, the information can be received from other sources associated with the device. For example, it may be received directly from the eye care practitioner's office, or from a GPS enabled cell phone. Software in the GPS enabled cell phone, for example using a Smartphone App can then record and send digital data, to the network or the ophthalmic lens storage unit, reflecting that the user was at the location as scheduled.

Figure 13:
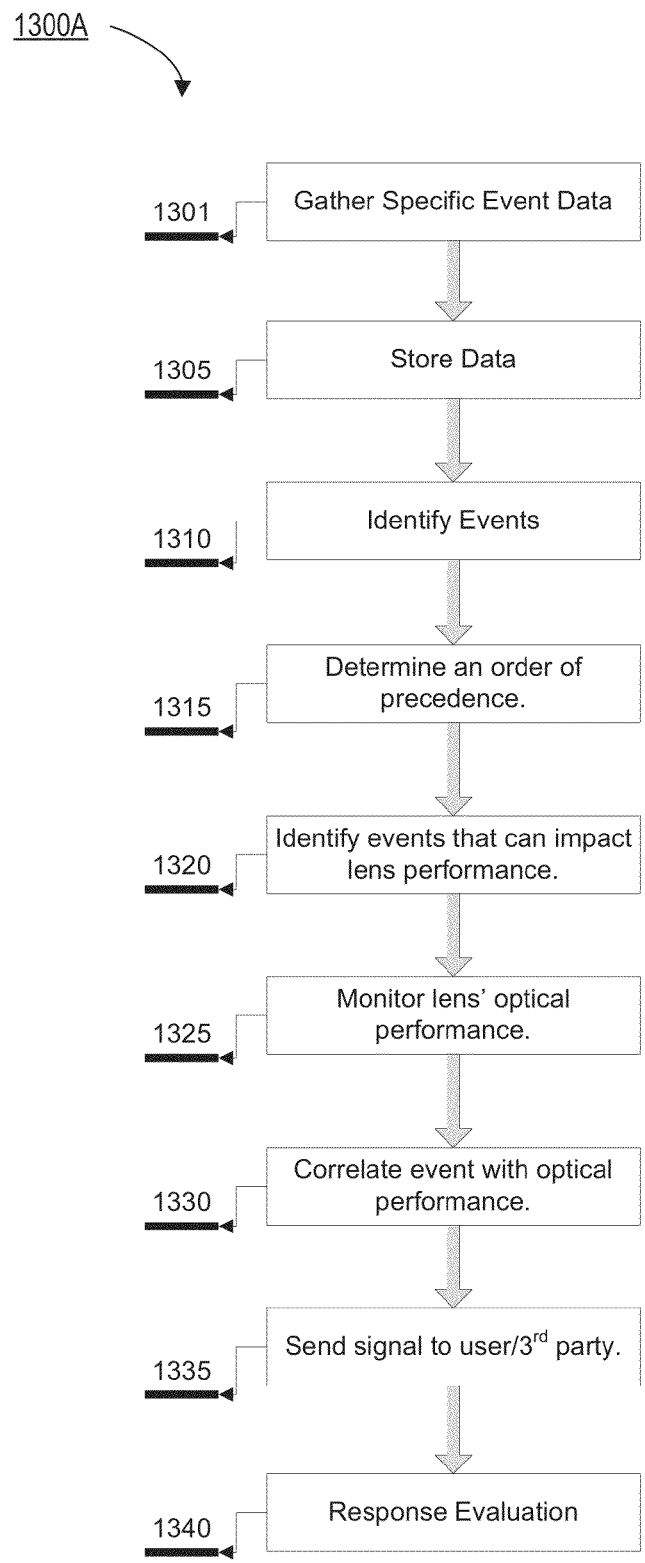
FIG. 13 illustrates a flowchart with exemplary steps a ophthalmic lens storage unit can implement to correlate events with changes in the optical performance of a lens.

Referring now to FIG. 13 a flowchart illustrates exemplary steps a ophthalmic lens storage unit can implement to correlate events with changes in the optical performance of a lens. At 1301, the system of the present invention can gather data continuously specific to each User's geographic location. The data may come into a server from direct or indirect inputs, from the User or from different non-users, through either one or an array of different Network Access Devices. At 1305, the data received in a consistent format and in real time can be supported by the system and may be stored in a designated database in the server. At 1310, the data received may be classified to identify/anticipate events in the life of the User which can have an effect with eye conditions or lens performance. After determining specific events, these Events may then be linked with different eye health and lens performance topics by the system using user specific data to determine an order of precedence for each event 1315. After the order of precedence determination, at 1320, the system can identify the most relevant events that can impact the performance of an ophthalmic lens and predict a lens condition. The lens can then be monitored 1325 by taking the data measured when the lens begins the cleaning cycle, during the cleaning cycle and at the end of the cleaning cycle to ensure optical performance is acceptable. When it is not optimal, the apparatus may correlate the event that caused the condition and alert the user or a third part 1335 by means of a message or a signal to prevent an eye infection or correct the condition that hinders optimal optical performance.

At 1340, the system can evaluate data from other users that have been subjected to the same conditions/events to increase the possibilities that the occurrence or non-occurrence of the condition/event was in fact what the system identified as the cause of the change in optical performance of the eye/lens. In addition, the evaluation can include a $3^{rd}$ party, such as a manufacturer of lenses, to gather all the data for analysis, to obtain records of product performance, and for product development.

CONCLUSION

The present invention, as described above and as further defined by the claims below, provides methods for collecting, storing and analyzing data for monitoring lens conditions, controlling case functions, displaying user messages, and programming an ophthalmic lens storage unit. Further, communication options allow data to be communicated between the ophthalmic lens storage unit and external devices or entities, through a network, for lens monitoring, automated ordering, and user's vision response to identified events/conditions.

While the above description contains many specificities, these should not be construed as limitations on the scope of any embodiment or method, but as exemplification of various embodiments thereof. Many other ramifications and variations are possible within the teachings of the various embodiments or methods. Thus, the scope should be determined by the appended claims and their legal equivalents, and not by the examples given.

The invention claimed is:

1. Apparatus for correlating geo-social phenomena to the condition of an ophthalmic lens, comprising:
    a programmable ophthalmic lens storage unit for storing one or more ophthalmic lenses, wherein the ophthalmic lens storage unit includes a processor in digital communication with a digital media storage device, wherein the digital media storage device stores executable software code;
    a transmitter and a receiver in logical communication with the processor and also in logical communication with a communication network, wherein the software is executable upon demand and operative with processor to;
    transmit and receive digital data via the transmitter and receiver;
    process stored digital data from one or more inputs and sources descriptive of a plurality of events;

determine an order of precedence of records descriptive of events, wherein the order of precedence is determined based upon events that have an impact in an ophthalmic lens' optic performance;

identify one or more events that can affect the optic performance of an ophthalmic lens;

monitor the optic performance of an ophthalmic lens in an ophthalmic lens storage unit;

correlate a change in the optic performance of the ophthalmic lens in the storage unit with the identified events; and transmit one or more signals to a predetermined network access device based upon the correlation of an event and the change in optical performance of the ophthalmic lens.

2. The apparatus of claim 1, wherein correlation data is stored in one or more of the sources.

3. The apparatus of claim 2, wherein the software is additionally operative to evaluate the correctness of the correlation by comparing the optical performance data of other ophthalmic lenses subjected to the same events in comparison to the data of the ophthalmic lens storage unit.

4. The apparatus of claim 1, wherein the software is additionally operative allow additional inputs to influence the order of precedence.

5. The apparatus of claim 1, additionally comprising one or more sensors for measuring and storing digital data descriptive of the ophthalmic lens' optical performance.

6. The apparatus of claim 5, wherein the sensor comprises a device to detect one or both of an intensity and a direction of vectors of light to generate data descriptive of optical properties of the ophthalmic lens during disinfection.

7. The apparatus of claim 5, additionally comprising a bar code reader capable of downloading and processing corresponding data that identifies an ophthalmic lens product through a network.

8. The apparatus of claim 7, wherein the corresponding data comprises optical performance specifications specific to the lens.

9. The apparatus of claim 8, wherein the data descriptive of the optical performance specifications of the ophthalmic lens includes optical power and base curve of the lens.

10. The apparatus of claim 9, wherein the measured optical performance is compared to the lens specifications to monitor actual optical performance of the ophthalmic lens.

11. The apparatus of claim 10, wherein the actual optical performance data measured is stored during disinfection for future analysis to detect changes in performance over time using predetermined thresholds.

12. The apparatus of claim 11, wherein the processor in the ophthalmic lens storage unit processes data descriptive of particle buildup at the beginning of a disinfecting cycle of the ophthalmic lens to diagnose an eye infection.

13. The apparatus of claim 5 wherein the sensor comprises a device to measure a temperature of a liquid in which the lens is stored.

14. The apparatus of claim 1 additionally comprising a user interface capable of displaying message reminders to the user based upon digital data transmitted by the processor.

15. The apparatus of claim 1 wherein the transmitted signals comprise communication elements capable of sending messages to an associated processing device used for receiving the messages and displaying the messages to one or both the user and a third party.

16. The apparatus of claim 1, wherein the events are specific to the location of the user.

17. The apparatus of claim 16, wherein the location of the user is determined by tracking the location of the storage unit.

18. The apparatus of claim 16, wherein the location of the user is determined through the use of an application in a handheld device.

19. The apparatus of claim 1, wherein the events include changes in atmospheric conditions.

20. The apparatus of claim 19, wherein the atmospheric conditions include temperature changes.

21. The apparatus of claim 19, wherein the atmospheric conditions include humidity changes.

22. The apparatus of claim 19, wherein the atmospheric conditions include atmospheric pressure changes.

23. The apparatus of claim 19, wherein the atmospheric conditions include tracking the presence of allergy-inducing particles in the air.

24. The apparatus of claim 1, additionally comprising a universal serial bus connector for providing logical communication between one or both of the processor and the digital storage, and a processing device.

25. The apparatus of claim 1 additionally comprising an electrical storage for storing power to operate the storage unit.

26. The apparatus of claim 25 wherein the electrical storage comprises one or more rechargeable batteries.

27. The apparatus of claim 26 wherein the electrical storage comprises one or more lithium batteries.

* * * * *